(12) United States Patent
Suh et al.

(10) Patent No.: US 9,366,635 B2
(45) Date of Patent: Jun. 14, 2016

(54) OPTICAL BIOSENSOR AND METHOD OF OPERATING THE SAME

(71) Applicant: Samsung Electronics Co., Ltd., Suwon-Si, Gyeonggi-Do (KR)

(72) Inventors: Sung-dong Suh, Seoul (KR); Kyoung-won Na, Seoul (KR); Yoon-dong Park, Osan-si (KR); Dong-mo Im, Jindo-gun (KR); Ju-hwan Jung, Seoul (KR); Seok-yong Hong, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 109 days.

(21) Appl. No.: 14/190,243

(22) Filed: Feb. 26, 2014

(65) Prior Publication Data
US 2014/0268165 A1 Sep. 18, 2014

(30) Foreign Application Priority Data

Mar. 13, 2013 (KR) ........................ 10-2013-0026807

(51) Int. Cl.
*G01B 9/02* (2006.01)
*G01N 21/77* (2006.01)

(52) U.S. Cl.
CPC ........ *G01N 21/77* (2013.01); *G01N 2021/7789* (2013.01)

(58) Field of Classification Search
CPC ....... G01N 21/77; G01N 21/17; G01N 21/45; G01N 2021/7789; G01J 2009/00; G01J 2009/002; G01J 2009/02; G01J 2009/0249; G01J 2009/0273
USPC .......................................................... 356/480
See application file for complete search history.

(56) References Cited

U.S. PATENT DOCUMENTS

| | | |
|---|---|---|
| 4,422,331 A | 12/1983 | Walker |
| 4,454,418 A | 6/1984 | Walker |
| 5,262,842 A * | 11/1993 | Gauglitz ............ G01N 21/7703 356/477 |
| 6,721,053 B1 | 4/2004 | Maseeh |
| 7,084,974 B1 | 8/2006 | Barwicz et al. |
| 7,446,880 B2 | 11/2008 | Vollmer et al. |

(Continued)

FOREIGN PATENT DOCUMENTS

| | | |
|---|---|---|
| EP | 1918693 A1 | 5/2008 |
| KR | 101160774 B1 | 6/2012 |

*Primary Examiner* — Tarifur Chowdhury
*Assistant Examiner* — Jonathon Cook
(74) *Attorney, Agent, or Firm* — Harness, Dickey & Pierce PLC

(57) ABSTRACT

An optical biosensor may include a biosensing unit, detection unit, and signal processing unit. The biosensing unit may be configured for receiving first and second optical signals (which are generated from a phase-modulated optical signal), outputting a sensing signal by transmitting the first optical signal via a first optical path that includes a sensing resonator, and outputting a reference signal by transmitting the second optical signal via a second optical path that includes a reference resonator. The detection unit may be configured for receiving the sensing signal and the reference signal, detecting a phase element of each of the sensing signal and the reference signal through a signal demodulation operation, and detecting a phase difference between the sensing signal and the reference signal according to the detected phase elements. The signal processing unit may be configured for calculating the concentration of a bio-material based on the detected phase difference.

18 Claims, 12 Drawing Sheets

(56) References Cited

U.S. PATENT DOCUMENTS

| | | |
|---|---|---|
| 7,483,144 B2 | 1/2009 | Sanders |
| 2003/0043428 A1 | 3/2003 | Lidsky et al. |
| 2010/0165351 A1 | 7/2010 | Xu et al. |
| 2013/0107257 A1* | 5/2013 | Goodno ................ H01S 3/2383 356/364 |

* cited by examiner

OPTICAL BIOSENSOR AND METHOD OF OPERATING THE SAME

CROSS-REFERENCE TO RELATED APPLICATION

This application claims priority under 35 U.S.C. §119 to Korean Patent Application No. 10-2013-0026807, filed on Mar. 13, 2013 in the Korean Intellectual Property Office, the disclosure of which is incorporated herein in its entirety by reference.

BACKGROUND

The present disclosure relates to a biosensor and a method of operating the same. The biosensor may be an optical biosensor for measuring the concentration of a bio-material based on an optical phenomenon.

A biosensor is a device for measuring the concentration of an organic or inorganic material in a liquid or gas state. A conventional biosensor includes a piezoelectric biosensor, an optical biosensor, and an electrochemical biosensor. An optical biosensor is a device for measuring the concentration of a bio-material, which is obtained when a biological element interacts with a material to be detected, based on an optical phenomenon. The concentration of a bio-material is measured by analyzing a shift in a resonant wavelength.

Conventionally, a shift in a resonant wavelength was observed by analyzing an optical signal using an optical spectrum analyzer (OSA). The OSA is formed of a measuring device, an optical packaging element, and the pertinent associated structures. Thus, a size of the OSA is generally relatively large, and it may be a challenge to integrate the OSA into a biosensor. Accordingly, downsizing a biosensor may be difficult based on the conventional art.

SUMMARY

Some embodiments relate to an optical biosensor, which is relatively easy to carry, and a method of operating the same. Mobility may be attained by integrating an element for analyzing a change in a resonant wavelength into the biosensor and downsizing the biosensor.

An optical biosensor may include a biosensing unit, a detection unit, and a signal processing unit. The biosensing unit may be configured for receiving first and second optical signals originating from a phase-modulated optical signal, outputting a sensing signal by transmitting the first optical signal via a first optical path that includes a sensing resonator, and outputting a reference signal by transmitting the second optical signal via a second optical path that includes a reference resonator. The detection unit may be configured for receiving the sensing signal and the reference signal, detecting a first phase element of the sensing signal and a second phase element of the reference signal through a signal demodulation operation, and detecting a phase difference between the sensing signal and the reference signal according to the detected first and second phase elements. The signal processing unit may be configured for calculating the concentration of a bio-material based on the detected phase difference or delay.

The first optical signal and the second optical signal may have the same phase.

When the bio-material is combined with the sensing resonator, a resonant wavelength of the sensing resonator may be changed, and the calculated phase difference may have a value that corresponds to an amount of a changed resonant wavelength of the sensing resonator.

The optical biosensor may further include a modulation unit for generating a modulation signal that has a phase which is in quadrature (or orthogonal) with respect to the sensing signal and the reference signal. The modulation signal may be provided to the detection unit.

The detection unit may receive a first modulation signal and a second modulation signal from the modulation unit, detect a first phase element of the sensing signal by performing a first operation on the sensing signal and the first modulation signal, and detect a second phase element of the reference signal by performing a second operation on the reference signal and the second modulation signal.

The optical biosensor may further include a light source for generating an optical signal; and an interferometer for receiving the optical signal and modulating a phase of the optical signal to generate the phase-modulated optical signal.

The optical biosensor may further include a database unit for storing information regarding the concentration of the bio-material in correspondence with the detected phase difference.

A method of operating an optical biosensor may include receiving first and second optical signals originating from a phase-modulated optical signal; outputting a sensing signal by transmitting the first optical signal via a first optical path that includes a sensing resonator; outputting a reference signal by transmitting the second optical signal via a second optical path that includes a reference resonator; detecting a first phase element of the sensing signal and a second phase element of the reference signal through a signal demodulation operation on the sensing signal and the reference signal; detecting a phase difference between the sensing signal and the reference signal according to the detected first and second phase elements; and calculating the concentration of a bio-material, based on the detected phase difference.

BRIEF DESCRIPTION OF THE DRAWINGS

Example embodiments of the present disclosure may be more clearly understood when the following detailed description is taken in conjunction with the accompanying drawings in which.

DETAILED DESCRIPTION

Figure 1:
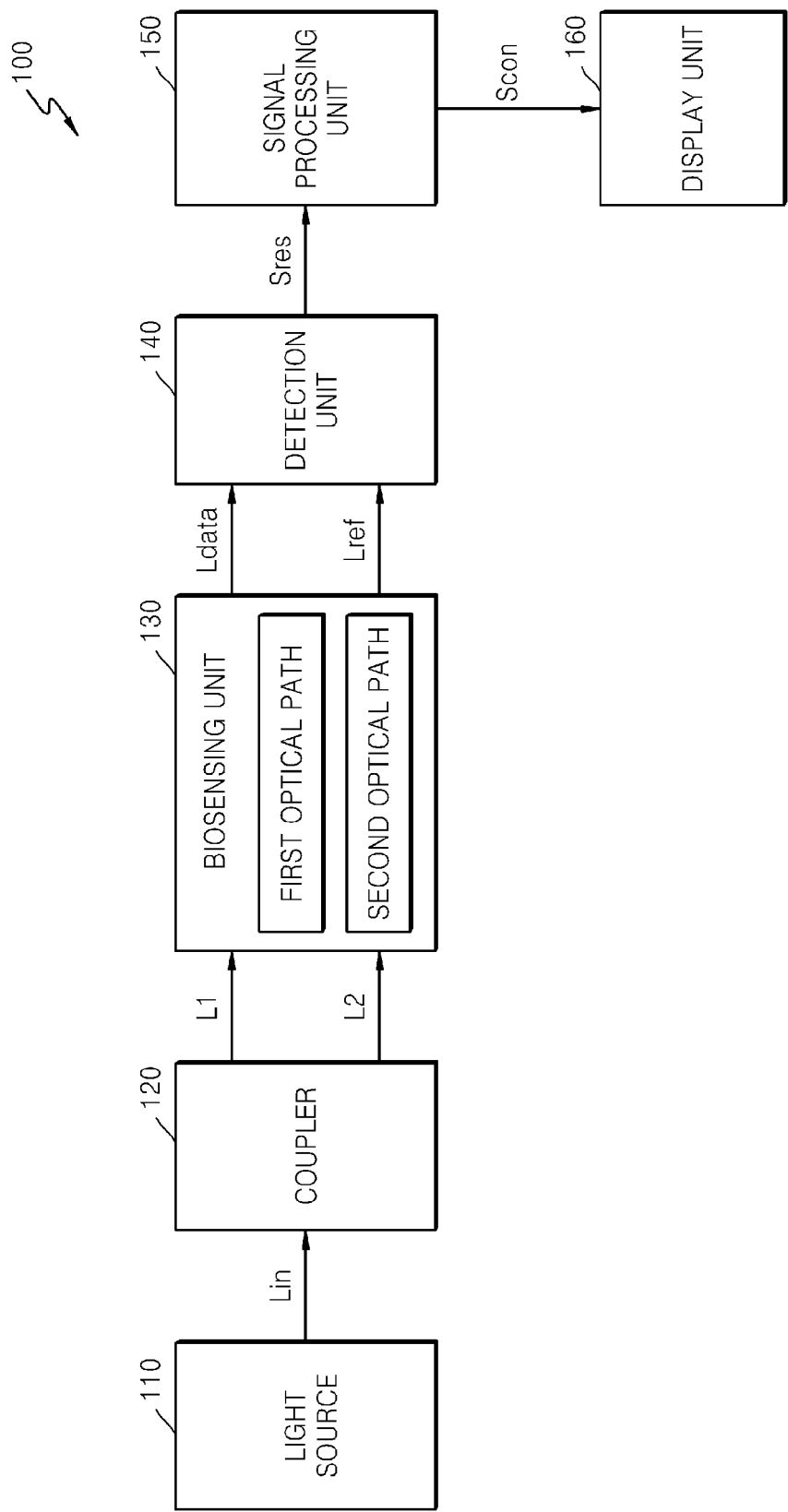
FIG. 1 is a block diagram illustrating an optical biosensor according to an example embodiment.

It will be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It will be understood that, although the terms first, second, third, etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of example embodiments.

Spatially relative terms, e.g., "beneath," "below," "lower," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms, "comprises," "comprising," "includes," and/or "including," if used herein, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 is a block diagram illustrating an optical biosensor 100 according to an example embodiment.

Referring to FIG. 1, the optical biosensor 100 may include a biosensing unit 130. The optical biosensor 100 may further include a processing element for processing an optical signal, and thus, reading the concentration of a bio-material. For example, the optical biosensor 100 may further include a detection unit 140 and a signal processing unit 150. Additionally, the optical biosensor 100 may further include a light source 110 and a coupler 120. The optical biosensor 100 may identify whether a bio-material exists and/or may measure the concentration of a bio-material, based on an optical phenomenon that results from an interaction between bio-materials, more particularly, a combination of a target material, for example, a target deoxyribonucleic acid (DNA) or an antigen, and a probe material, for example, a probe DNA or an antibody.

The light source 110 generates an input optical signal $L_{in}$, and the generated input optical signal $L_{in}$ may be provided to the biosensing unit 130 via the coupler 120. The input optical signal $L_{in}$ is a signal that is generated by phase-modulating a general optical signal. The input optical signal $L_{in}$ may be separated into a first optical signal L1 and a second optical signal L2 via the coupler 120 and before being provided to the biosensing unit 130. Before passing through a resonator (not illustrated) included in the biosensing unit 130, the first optical signal L1 and the second optical signal L2 may have the same phase. FIG. 1 illustrates that the light source 110 is included in the optical biosensor 100, and the light source 110 generates a phase-modulated input optical signal $L_{in}$. However, the present disclosure is not limited thereto. For example, the optical biosensor 100 may receive a phase-modulated optical signal from an external source, without having to include the light source 110.

The biosensing unit 130 may transmit an optical signal via two or more optical paths. For example, the biosensing unit 130 may include a first optical path via which a first optical signal L1 is transmitted, and a second optical path via which a second optical signal L2 is transmitted. The first and second optical paths may each include a resonator, for example, a ring resonator. The first optical path of the biosensing unit 130 may include a sensing resonator, and the second optical path may include a reference resonator.

The biosensing unit 130 may generate a sensing signal Ldata, which has a wavelength that is changed according to a sensing of a bio-material, and a reference signal Lref, which has a reference wavelength. As an example, as the first optical signal L1 passes through the sensing resonator, the sensing signal Ldata may be generated. As the second optical signal L2 passes through the reference resonator, the reference signal Lref may be generated. The sensing signal Ldata may be an optical signal that is obtained when a resonant wavelength, which is shifted according to the concentration of a bio-material, is extracted or lost from a wavelength element of the first optical signal L1.

As the sensing signal Ldata and the reference signal Lref respectively pass through resonators that respectively have different resonance wavelengths, the sensing signal Ldata and the reference signal Lref have different phases. The sensing signal Ldata and the reference signal Lref are provided to the detection unit 140. The detection unit 140 respectively detects a phase element of each of the sensing signal Ldata and the reference signal Lref, through a demodulation operation. The detection unit 140 also detects a phase delay (or, the phase delay may be referred as a phase difference) between the sensing signal Ldata and the reference signal Lref. A detection result signal Sres is provided to the signal processing unit 150. By analyzing the detection result signal Sres, the signal processing unit 150 calculates an amount of a shifted resonant wavelength of the sensing resonator. Additionally, the signal processing unit 150 outputs a concentration sensing signal Scon of a bio-material according to the calculated amount of a shifted resonant wavelength. A measured value of concentration of a material, according to the concentration sensing signal Scon, is displayed on the display unit 160.

The biosensing unit 130 and the detection unit 140 may be formed or packaged on the same substrate. According to another example embodiment, the biosensing unit 130, the detection unit 140, and/or the signal processing unit 150 may be formed or packaged on the same substrate. According to another example embodiment, the light source 110, the coupler 120, the biosensing unit 130, the detection unit 140, and/or the signal processing unit 150 may be formed or packaged on the same substrate.

The concentration of a bio-material may be measured by detecting a phase delay between the sensing signal Ldata and the reference signal Lref, without having to utilize an additional device, such as a spectrometer. Thus, the detection unit 140 and the signal processing unit 150 may be integrated into the optical biosensor 100 with relative ease. Accordingly, the optical biosensor 100 may be downsized with relative ease. As a result, the optical biosensor 100 may be formed to interwork with a mobile smart device.

Figure 2:
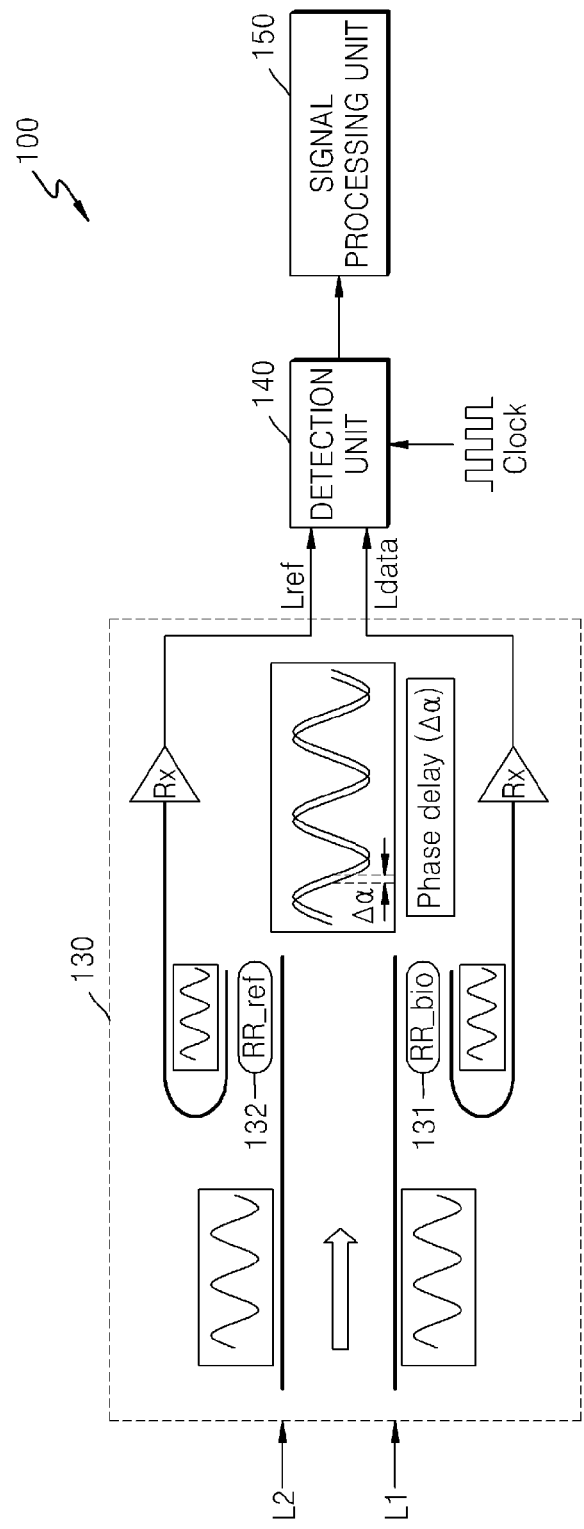
FIG. 2 is a block diagram illustrating an example of implementation of the optical biosensor of FIG. 1.

FIG. 2 is a block diagram illustrating an example of implementation of the optical biosensor 100 of FIG. 1. For convenience of description, FIG. 2 illustrates the biosensing unit 130, the detection unit 140, and the signal processing unit 150.

Referring to FIGS. 1 and 2, the phase-modulated input optical signal $L_{in}$ may be separated into the first optical signal L1 and the second optical signal L2 via the coupler 120. The first optical signal L1 passes through a first optical path that includes a sensing resonator 131. The second optical signal L2 passes through a second optical path that includes a reference resonator 132. FIG. 2 illustrates an example in which both the sensing resonator 131 and the reference resonator 132 are implemented as a ring resonator. However, it should be understood that a different type of resonator may be used. Before passing through the ring resonator, the first optical signal L1 and the second optical signal L2 may have the same phase. In each of the first and second optical paths, one or more buffers for transmitting an optical signal may be further included.

As the first optical signal L1 and the second optical signal L2 pass through their respective ring resonators, a difference between the first and second optical paths, which the first optical signal L1 and the second optical signal L2 respectively pass through, may be substantially generated according to a changed amount of the effective index. Accordingly, the sensing signal Ldata and the reference signal Lref may have a phase change that corresponds to the changed amount of the effective index. Thus, by detecting a phase delay Δα, between the sensing signal Ldata and the reference signal Lref, a shifted amount of a resonant wavelength of the sensing resonator 131, according to a bio-material, may be calculated.

The detection unit 140 receives the sensing signal Ldata and the reference signal Lref, and performs a demodulation operation for extracting a phase on each of the sensing signal Ldata and the reference signal Lref. According to a demodulation result, the detection unit 140 analyzes the extracted phase, and thus, detects a phase delay between the sensing signal Ldata and the reference signal Lref. The detection unit 140 may further receive a clock signal that has a known, desired, and/or predetermined frequency. By obtaining a counting result (based on the clock signal) that corresponds to the phase delay between the sensing signal Ldata and the reference signal Lref, the detection unit 140 may output a signal in which a phase delay is reflected. Based on a detection result, the signal processing unit 150 may calculate an amount of the shifted resonant wavelength of the sensing resonator 131. Then, according to a calculation result, the signal processing unit 150 may calculate the concentration of the bio-material.

Figure 3:
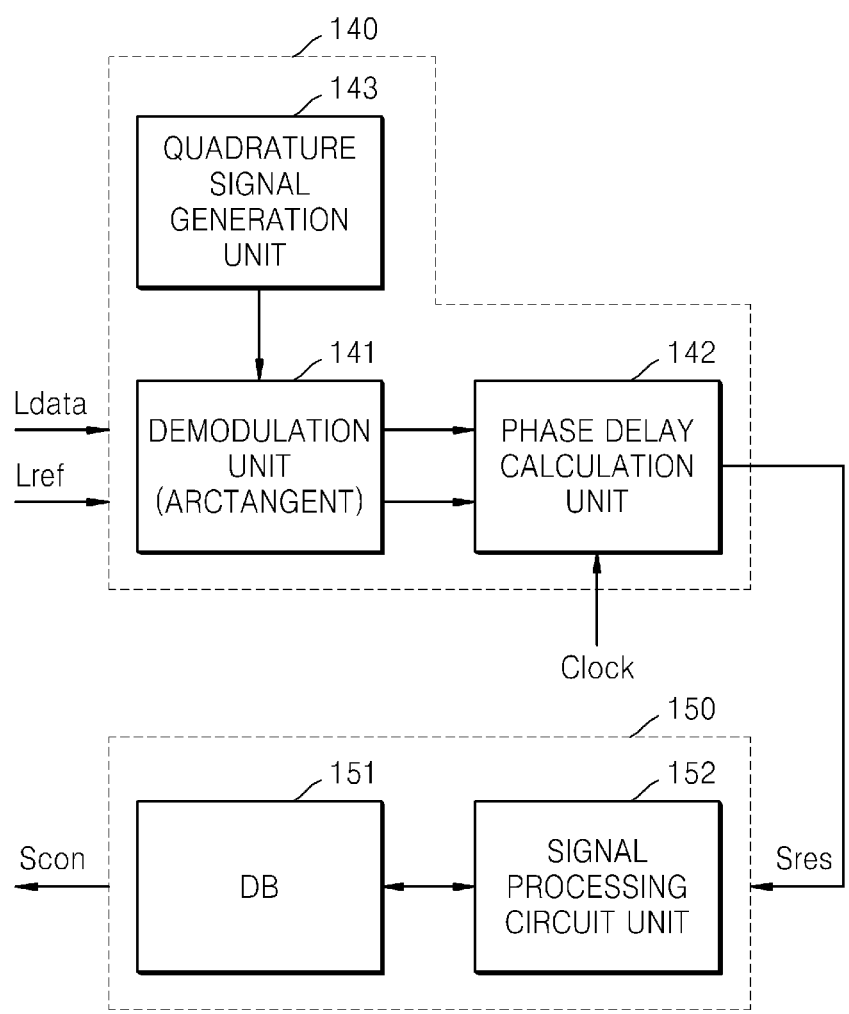
FIG. 3 is a block diagram illustrating an example of implementation of a detection unit and a signal processing unit which are shown in FIG. 1.

FIG. 3 is a block diagram illustrating an example of implementation of the detection unit 140 and the signal processing unit 150 of FIG. 1. As illustrated in FIG. 3, the detection unit 140 may include a demodulation unit 141, a phase delay calculation unit 142, and a quadrature signal generation unit 143. Additionally, the signal processing unit 150 may include a database 151 and a signal processing circuit unit 152.

Referring to FIGS. 1 through 3, if the phase-modulated input optical signal $L_{in}$ is assumed as an input optical signal I, the input optical signal I may have signal characteristics according to an equation which is shown below. As shown in Equation 1, the input optical signal I may have a known, desired, and/or predetermined amplitude. A change in the input optical signal I may follow a cosine (cos) function, and a phase in the input optical signal I varies with a shift in a wavelength λ. The first optical signal L1 and the second optical signal L2, which are generated via the coupler 120, may also follow the cosine function which is shown below.

$$I = AI_0\left[1 + \cos\left(\frac{2\pi d}{\lambda}\right)\right] \quad \text{[Equation 1]}$$

As the first optical signal L1 and the second optical signal L2 respectively pass through their ring resonators (which have different resonant wavelengths), a wavelength of the sensing signal Ldata may be different from a wavelength of the reference signal Lref. Accordingly, a difference in a phase element thereof may be generated. By detecting a phase element or a wavelength element from each of the sensing signal Ldata and the reference signal Lref, a phase delay therebetween may be detected. As the input optical signal I is processed by using the phase-modulated optical signal, a modulation operation of the optical signal is performed.

The demodulation unit 141 receives the sensing signal Ldata and the reference signal Lref, and performs a modulation operation for generating a linear output for a shift in each signal wavelength. The modulation operation may be performed based on a quadrature signal processing in a time domain. Accordingly, through the demodulation operation, a phase element of each of the sensing signal Ldata and the reference signal Lref may be extracted.

An arctangent modulation operation may be performed as a modulation operation. To do so, a signal processing may be performed by using a quadrature signal. If the sensing signal Ldata and the reference signal Lref respectively follow a cosine function, the quadrature signal generation unit 143 may generate a signal that follows a sine (sin) function. The demodulation unit 141 may divide a signal, which follows a sin function, into the sensing signal Ldata and the reference signal Lref that respectively follow a cosine function. The demodulation unit 141 may also perform an arctangent modulation operation on a signal which is generated by performing an operation on the dividing of the signal into the sensing signal Ldata and the reference signal Lref. Accordingly, a phase element of each of the sensing signal Ldata and the reference signal Lref is extracted.

The phase delay calculation unit 142 calculates a phase delay between the sensing signal Ldata and the reference signal Lref from a phase element of the extracted sensing signal Ldata and the reference signal Lref. For example, the phase delay calculation unit 142 may receive a clock signal that has a known, desired, and/or predetermined frequency. By counting the number of clocks of a clock signal in a period that corresponds to the phase delay of the sensing signal Ldata and the reference signal Lref, the phase delay calculation unit 142 may generate a detection result signal Sres, which represents information about the phase delay.

The signal processing circuit unit 152 determines the concentration of a bio-material in response to a detection result signal Sres, which is generated from the detection unit 140, and outputs a resultant concentration sensing signal Scon. The signal processing unit 150 may include the database 151, as well as the signal processing circuit unit 152. Data regarding various bio-materials may be stored in the database 151. Additionally, data regarding the concentration of bio-materials, according to a value of a phase delay, may be stored in the database 151. As an example, information regarding the concentration of bio-materials, according to a value of a phase delay between the sensing signal Ldata and the reference signal Lref, may be databased and stored in the database 151. Concentration information, which corresponds to the detection result signal Sres, is output from the database 151. Based on the concentration information, a concentration sensing signal Scon, which represents a result of sensing a bio-material, may be generated.

Figure 4:
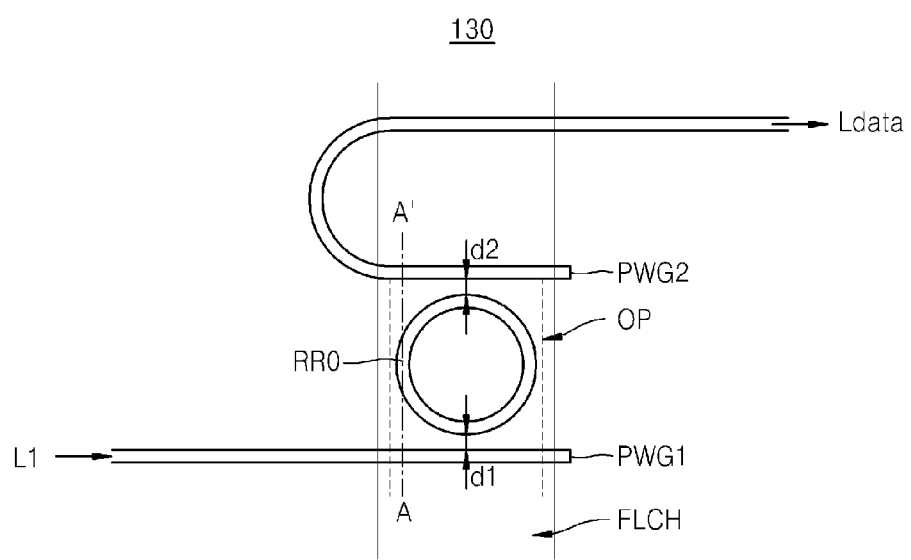
FIG. 4 is a diagram illustrating an example of implementation of a biosensing unit of FIG. 2.

FIG. 4 is a diagram illustrating an example of implementation of the biosensing unit 130 of FIG. 2. FIG. 4 illustrates an example of implementation of the sensing resonator 131, which is included in a first optical path of the biosensing unit 130, and waveguides, which correspond to the biosensing unit 130. Additionally, the reference resonator 132, which is in a second optical path, and waveguides may also be implemented identically or similarly to those shown in FIG. 4.

Referring to FIG. 4, the first optical path of the biosensing unit 130 may include a first optical wave guide PWG1, a ring resonator RR0, and a second optical waveguide PWG2. The ring resonator RR0 may correspond to the sensing resonator 131. A fluidic channel FLCH may be located on an upper part of the first optical wave guide PWG1, the ring resonator RR0, and the second optical waveguide PWG2. In an upper part of the ring resonator RR0, an opening OP exposing the ring resonator RR0 in the fluidic channel FLCH may be formed. The first and second optical waveguides PWG1 and PWG2 may be a linear optical waveguide. The ring resonator RR0 may be an optical waveguide in a shape of a circle or in the form of a race track.

The ring resonator RR0 may be placed with a first gap d1 between the ring resonator RR0 and the first optical waveguide PWG1, and the ring resonator RR0 may be placed with a second gap d2 between the ring resonator RR0 and the second optical waveguide PWG2. The ring resonator RR0 may be placed horizontally with respect to the first optical waveguide PWG1, with the first gap d1 therebetween, and placed horizontally with respect to the second optical waveguide PWG2, with the second gap d2 therebetween. Alternatively, the ring resonator RR0 may be placed vertically with respect to the first optical waveguide PWG1, with the first gap d1 therebetween, and placed vertically with respect to the second optical waveguide PWG2, with the second gap d2 therebetween.

Although not illustrated in FIG. 4, a ring resonator may be disposed in the second optical path, via which the second optical signal L2 is transmitted, as the reference resonator 132. First and second optical waveguides may be disposed with a desired or predetermined gap between the first and second optical waveguides, and the ring resonator.

Figure 5A:
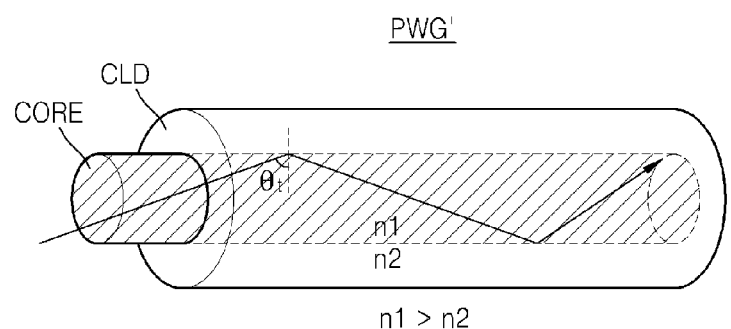
FIGS. 5A and 5B illustrates examples of optical waveguides which may be included in the biosensing unit of FIG. 4.
Figure 5B:
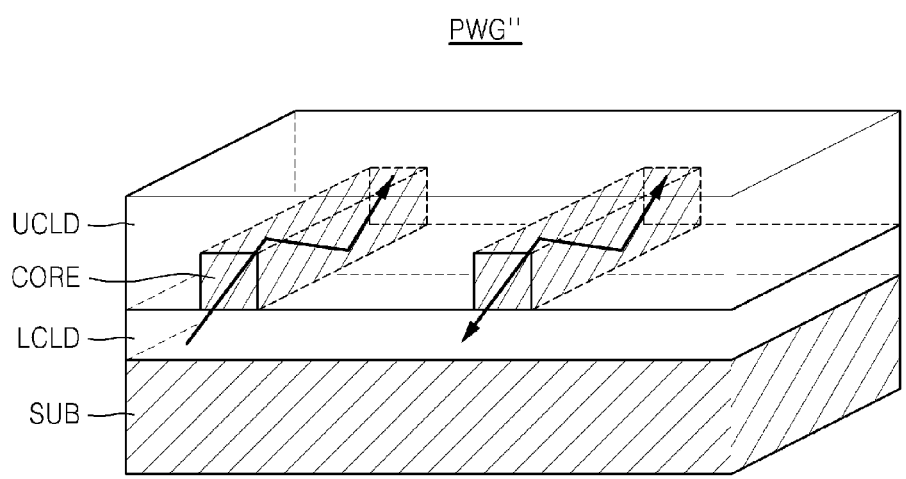

FIGS. 5A and 5B illustrate examples of optical waveguides which may be included in the biosensing unit 130 of FIG. 4.

Referring to FIG. 5A, an optical waveguide PWG' may include a core CORE via which an optical signal is propagated and a cladding CLD that surrounds the core CORE. A refractive index n1 of the core CORE is higher than a refractive index n2 of the cladding CLD. Accordingly, if an optical signal is incident on the core CORE with an angle θt of a threshold value or higher, the optical signal is not transmitted to the outside, and may be guided to proceed along the core CORE.

Referring to FIG. 5B, an optical waveguide PWG" may be implemented as a silicon waveguide which is formed on a semiconductor substrate SUB. A lower cladding layer LCLD is formed on the semiconductor substrate SUB, and a core layer CORE may be formed on the lower cladding layer LCLD. Additionally, an upper cladding layer UCLD, which surrounds the core layer CORE, may be formed. However, it should be understood that this is only an example embodiment. A configuration of the optical waveguide PWG" (e.g., an order in which each layer is formed and a shape of each layer) may be modified to have a form different from that shown.

The core layer CORE may include silicon (Si) or a Si-based compound, for example, silicon nitride (SiN). The lower cladding layer LCLD and the upper cladding layer UCLD may contain oxide (Ox). A refractive index of Si is about 3.5, and a refractive index of Ox is about 1.4. Thus, a refractive index of the core layer CORE is higher than those of the lower and upper cladding layers LCLD and UCLD. Accordingly, if an optical signal is incident on the core layer CORE with an angle of a critical value or higher, total reflection may be generated at a boundary of the core layer CORE and the lower and upper cladding layers LCLD and UCLD, and thus, an optical signal may propagate along the core layer CORE.

Referring back to FIG. 4, a wavelength that complies with a resonance condition of the ring resonator RR0 in a wavelength of the first optical signal L1 which passes through the first optical waveguide PWG1, that is, a resonant wavelength λr is transited to the ring resonator RR0 through total reflection. Then, the resonant wavelength λr is propagated via the ring resonator RR0, transited to the second optical waveguide PWG2, and then, output as a sensing signal Ldata.

Accordingly, the sensing signal Ldata, which is generated from the biosensing unit 130, may be an optical signal which is obtained by extracting a resonant wavelength λr from the first optical signal L1. The resonant wavelength λr may be shifted according to the concentration of a bio-material, which is detected by the biosensing unit 130. Accordingly, a wavelength element of the sensing signal Ldata may be changed according to the concentration of a bio-material.

More particularly, the opening OP, via which an external material, for example, a bio-material to be detected contacts, is formed on the ring resonator RR0. After a semiconductor device or circuit is formed on a semiconductor substrate, a passivation layer for protecting the semiconductor device or circuit from an external material may be formed. The opening OP may be formed by not applying a passivation material on an upper part of the ring resonator RR0. A fluid or a gas, which contains a bio-material, may flow into the fluidic channel FLCH that is located outside the optical biosensor 100 and contacts the opening OP, and may contact the ring resonator RR0 via the opening OP.

Figure 6A:
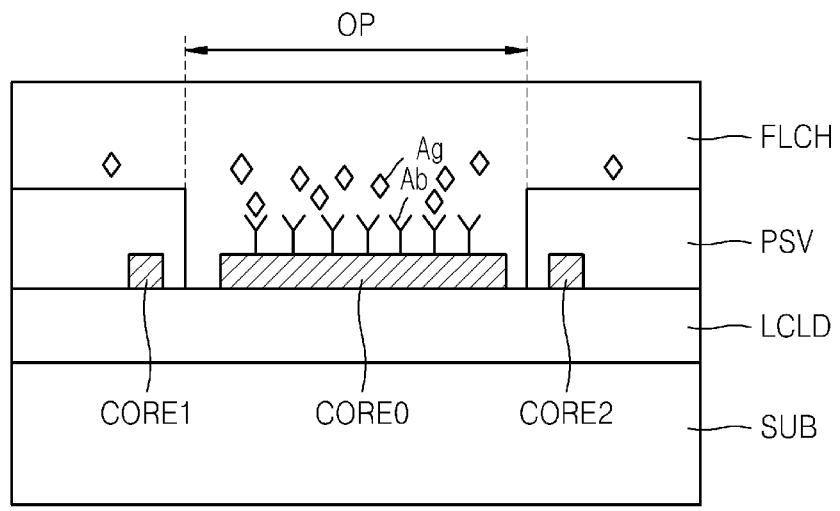
FIGS. 6A and 6B are cross-sectional views of the biosensing unit taken along line A-A' of FIG. 4.
Figure 6B:
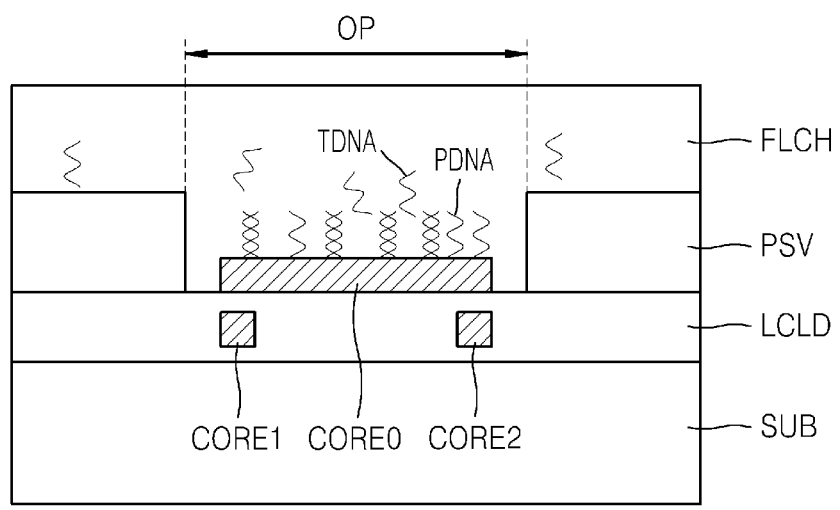

FIGS. 6A and 6B are cross-sectional views of the biosensing unit 130 taken along line A-A' of FIG. 4. FIG. 6A illustrates a case when a target material is DNA. FIG. 6B illustrates a case when a target material is an antigen.

Referring to FIG. 6A, a core layer CORE1 of the first optical waveguide PWG1, a core layer CORE2 of the second optical waveguide PWG2, and the core layer CORE0 of the ring resonator RR0 may be formed on the same layer and placed in a horizontal position. The ring resonator RR0 may be placed horizontally with respect to the first and second optical waveguides PWG1 and PWG2, with a desired or predetermined gap therebetween. On an upper part of the first and second optical waveguides PWG1 and PWG2, the passivation layer PSV may be formed. In an upper part of the ring resonator RR0, the opening OP, instead of the passivation layer PSV, may be formed.

Referring to FIG. 6B, the core layers CORE1 and CORE2 of the first and second optical waveguides PWG1 and PWG2 are formed on a lower layer, for example, an inside of the lower cladding layer LCLD. The core layer CORE0 of the ring resonator RR0 may be formed on an upper layer, for example, on an upper part of the lower cladding layer LCLD. Likewise, the core layers CORE1 and CORE2 of the first and second optical waveguides PWG1 and PWG2, and the core layer CORE0 of the ring resonator RR0 may be formed on different layers, and placed vertically with respect to each other. The ring resonator RR0 may be placed vertically with respect to the first and second optical waveguides PWG1 and PWG2, with a desired or predetermined gap therebetween.

Referring to FIGS. 6A and 6B, a receptor according to a target material (or, the target material may be referred as a bio-material to be measured) is fixed on a surface of the core layer CORE0 of the ring resonator RR0. The receptor may be fixed on a surface of the core layer CORE0 of the ring resonator RR0 by using a biological or physical and chemical method. In the example shown in FIG. 6A, the target material is an antigen Ag, and a receptor is an antibody Ab. In the example shown in FIG. 6B, the target material is a DNA, which is a target DNA (TDNA), and a receptor is a probe DNA (PDNA).

If a target material, that is, a bio-material which is an antigen Ag or a TDNA is combined with a receptor which is an antibody Ab or a PDNA, an effective index of the core layer CORE0 of the ring resonator RR0 is changed. Thus, a resonant wavelength λr of the ring resonator RR0 may be shifted according to the effective index of the core layer CORE0. The resonant wavelength λr may be expressed as shown in Equation 2.

$$\lambda r = neff 2\pi R/m \quad \text{[Equation 2]}$$

where $n_{eff}$ is an effective index, R is a radius of the ring resonator RR0, and m is an integer. Referring to Equation 2, a resonant wavelength λr is proportional to the effective index $n_{eff}$. Accordingly, if the effective index $n_{eff}$ increases or decreases, the resonant wavelength λr of the ring resonator RR0 may be increased or decreased.

For example, before the receptor Ab or PDNA and the bio-material Ag or TDNA are combined, an effective index of the ring resonator RR0 is n0 and a resonant wavelength λr is λ0. When the receptor and the bio-material are combined, the effective index of the ring resonator RR0 increases to n1, n2, n3, . . . and the effective index of the resonant wavelength λr may be shifted to λ1, λ2, λ3, . . . . A degree, in which the receptor Ab or PDNA and the bio-material Ag or TDNA are combined, may vary with the concentration of the bio-material Ag or TDNA. Thus, the resonant wavelength λr may vary with the concentration of a bio-material.

On the contrary, a bio-material is not combined in a ring resonator corresponding to the reference resonator 132, which is disposed in a second optical path via which the second optical signal L2 is transmitted. Accordingly, a resonant wavelength of the ring resonator, which corresponds to the second optical signal L2 regardless of the concentration of a bio-material, is not shifted. The concentration of a bio-material may be analyzed by using a value of a difference between a resonant wavelength λr of a sensing ring resonator (with which a bio-material is combined) and a resonant wavelength of a reference ring resonator (which is not combined with a bio-material).

Figure 7A:
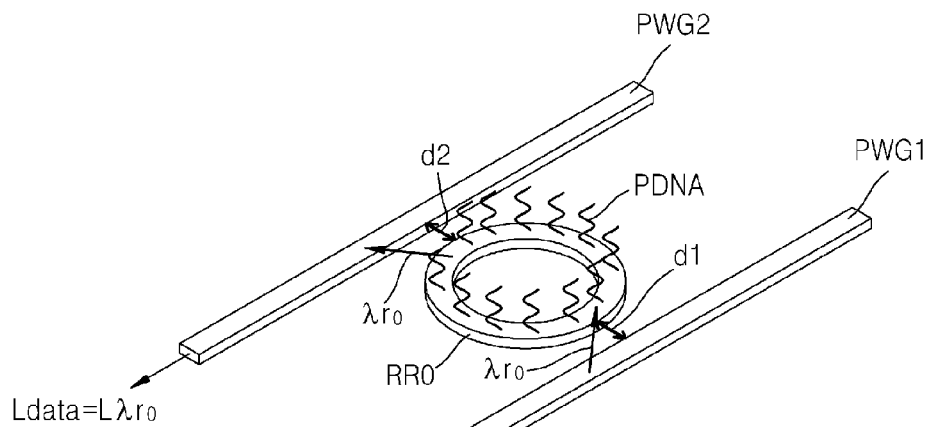
FIGS. 7A through 7C are diagrams illustrating statuses of the biosensing unit of FIG. 4, which respectively show a state before a target material and a probe material are combined, a state after a target material and a probe material are combined, and wavelength characteristics of a sensing signal.
Figure 7B:
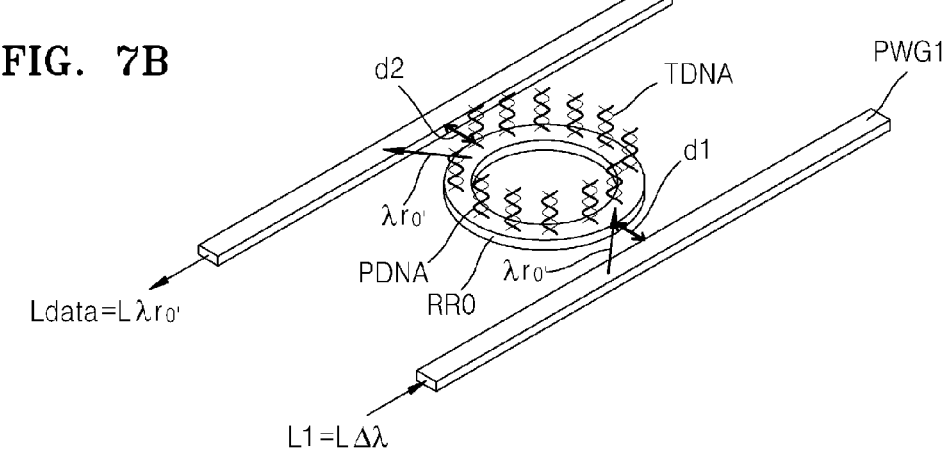
Figure 7C:
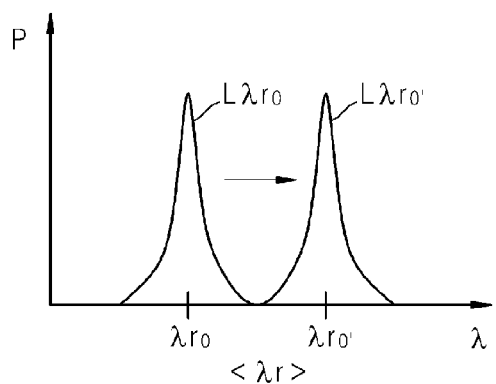

FIG. 7A illustrates a status of the biosensing unit 130 of FIG. 4 before a target material and a probe material are combined. FIG. 7B illustrates a status of the biosensing unit 130 of FIG. 4 after a target material and a probe material are combined. FIG. 7C illustrates wavelength characteristics of the sensing signal Ldata which is shown in FIGS. 7A and 7B.

Referring to FIG. 7A, when the first optical signal L1, which has a wavelength Δλ of a certain bandwidth, is incident on the first optical waveguide PWG1, the first optical signal L1 proceeds along the first optical waveguide PWG1. The resonant wavelength λr0, among the wavelength Δλ of the certain bandwidth, is transited to the ring resonator RR0 via the gap d1 between the first optical wavelength PWG1 and the ring resonator RR0. Additionally, the resonant wavelength λr0 is transited to the second optical wavelength PWG2 again via the gap d2 between the ring resonator RR0 and the second optical wavelength PWG2, and output as the sensing signal Ldata. If the PDNA and the TDNA are not combined, the resonant wavelength λr of the ring resonator RR0 is λr0. Assuming that the resonant wavelength λr is λr0 when the TDNA is not combined, in a case of the reference resonator, a resonant wavelength of the reference resonator may have the same value, that is, a value of λr0.

Referring to FIG. 7B, when the PDNA and the TDNA are combined, an effective index of the ring resonator RR0 is changed. Accordingly, the resonant wavelength is changed from λr0 to λr0'. Then, the effective index of the ring resonator RR0 is changed according to the concentration of the TDNA. Accordingly, the resonant wavelength may be shifted. Referring to FIG. 7C, as the resonant wavelength is shifted from λr0 to λr0' by combining the PDNA and the TDNA, the sensing signal Ldata is changed from Lλr0 to Lλr0'.

Figure 8A:
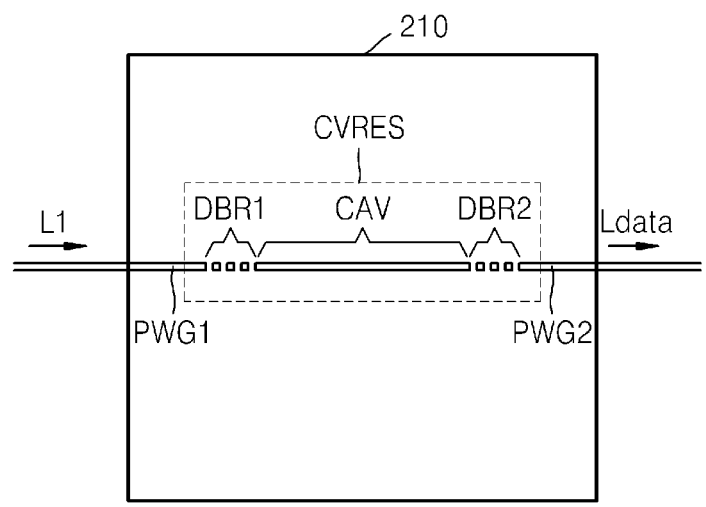
FIGS. 8A and 8B are diagrams illustrating various examples of implementation of a resonator and an optical waveguide.
Figure 8B:
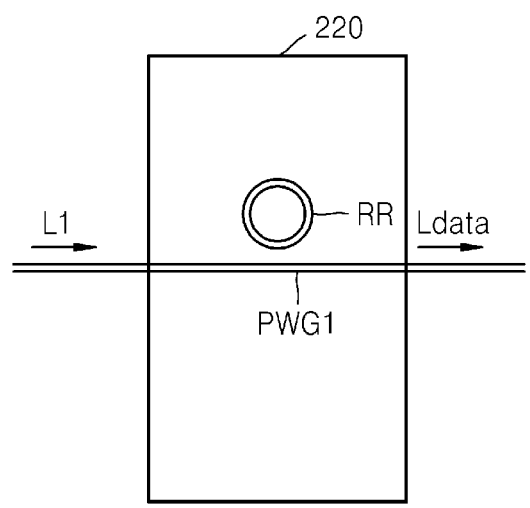

FIGS. 8A and 8B are diagrams illustrating various examples of implementation of a resonator and an optical waveguide. FIGS. 8A and 8B illustrate the resonator and the optical waveguide, which may be included in the first optical path via which the first optical signal L1 is transmitted. Additionally, a resonator and an optical waveguide, which are identical or similar to those illustrated in FIGS. 8A and 8B, may also be disposed in the second optical path (not illustrated) via which the second optical signal L2 is transmitted.

Referring to FIG. 8A, the biosensor unit 210 may include a resonator and an optical waveguide which are disposed in the first optical path, and include a resonator and an optical waveguide which are disposed in the second optical path (not illustrated). FIG. 8A illustrates a resonator and an optical waveguide which are disposed in the first optical path. The biosensor unit 210 receives the first optical signal L1, and thus, generates the sensing signal Ldata of which a wavelength is shifted according to the concentration of a biomaterial. The biosensor unit 210 may include the first optical waveguide PWG1, a cavity resonator CVRES, and the second optical waveguide PWG2.

The first optical waveguide PWG1 receives the first optical signal L1. The cavity resonator CVRES outputs a resonant wavelength, among a wavelength of the first optical signal L1, to the second optical waveguide PWG2 as the sensing signal Ldata.

The cavity resonator CVRES may include two distributed Bragg reflectors (DBRs) DBR1 and DBR2 and a cavity CAV. The DBRs DBR1 and DBR2 reflect a specific wavelength from among several wavelengths of the first optical signal L1. Accordingly, the two DBRs DBR1 and DBR2, and a cavity CAV are combined, and thus, function as a resonator. Additionally, a resonant wavelength, which complies with a resonance condition, is generated as the sensing signal Ldata and output.

An opening is formed in an upper part of the cavity CAV. A receptor, which corresponds to a bio-material to be measured, is attached to the upper part of the cavity CAV. According to a combining degree, that is, the concentration of a bio-material, an effective index of the cavity resonator CVRES may be changed. Accordingly, a resonant wavelength may be shifted according to the concentration of a bio-material, and thus, a wavelength element of the sensing signal Ldata may be changed.

FIG. 8B illustrates another example of implementation of a resonator and an optical waveguide. As illustrated in FIG. 8B, the biosensor unit 220 includes the first optical waveguide PWG1 and the ring resonator RR. The first optical waveguide PWG1 and the ring resonator RR are placed with a certain gap therebetween. When a receptor, which corresponds to a biomaterial of which the concentration is to be measured, is attached to a surface of a core of the ring resonator RR. If the receptor and the bio-material are combined, a resonant wavelength of the ring resonator is shifted according to a combining degree.

The first optical signal L1, which is incident on the first optical waveguide PWG1, proceeds along the first optical waveguide PWG1. A wavelength that complies with a resonance condition of the ring resonator RR among a wavelength of the first optical signal L1, that is, a resonant wavelength, is transited to the ring resonator RR. Accordingly, a sensing signal Ldata which is obtained when a resonant wavelength, among a wavelength of the first optical signal L1, is lost, and thus, is output via the first optical waveguide PWG1. A resonant waveguide of the ring resonator RR is shifted according to the concentration of a bio-material. Accordingly, a wavelength of the sensing signal Ldata may also be shifted according to the concentration of a bio-material.

Figure 9:
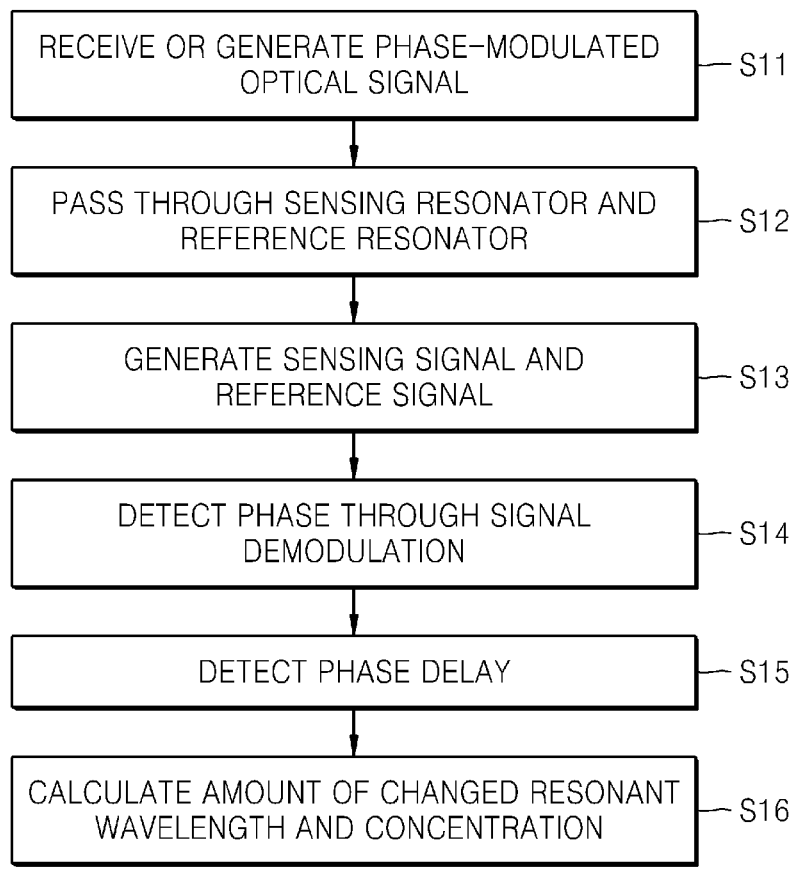
FIG. 9 is a flowchart illustrating a method of operating an optical biosensor according to an example embodiment.

FIG. 9 is a flowchart illustrating a method of operating an optical biosensor according to an example embodiment.

As illustrated in FIG. 9, in operation S11, an optical signal, which is externally phase-modulated, is received by an optical biosensor. Alternatively, an element, such as an interferometer, may be included inside the optical biosensor, and thus, a phase-modulated optical signal may be generated from an inside of the optical biosensor. Additionally, the optical biosensor includes a first optical path which includes a sensing resonator and a second optical path which includes a reference resonator. The phase-modulated optical signal is transmitted via the first optical path and the second optical path. The phase-modulated optical signal may be separated into a first optical signal and a second optical signal via a coupler.

In operation S12, the first optical signal passes through the sensing resonator, and the second optical signal passes through the reference resonator. A resonant wavelength of the sensing resonator may be shifted according to a degree in which a bio-material is combined. On the contrary, the reference resonator has the same resonant wavelength, regardless of a bio-material. Desirably, when a bio-material is not combined, a resonant wavelength of the sensing resonator may have the same value as a resonant wavelength of the reference resonator.

In operation S13, as the first optical signal passes through the sensing resonator, a sensing signal is generated. Additionally, as the second optical signal passes through the reference resonator, a reference signal is generated. Before passing through the resonators, the first optical signal and the second optical signal have substantially the same phase. However, after passing through the resonators, a sensing signal and a reference signal may have different phases. A phase delay between the sensing signal and the reference signal has a value which is relevant to the concentration of a bio-material which is combined with the sensing resonator.

In operation S14, a phase detection operation is performed based on a demodulation operation, with regard to a sensing signal and a reference signal. The demodulation operation may be performed by using a quadrature signal processing in a time domain. For example, with regard to a sensing signal and a reference signal, which have cosine function characteristics, respectively, an operation processing is performed by using a quadrature signal that has characteristics of a sine function. Then, a processing, such as an arctangent calculation, is performed. Thus, a phase element of the sensing signal and the reference signal may be detected.

In operation S15, the phase element (e.g., first phase element) of the sensing signal and the phase element (e.g., second phase element) of the reference signal are detected. Based on the phase elements, a phase delay between the sensing signal and the reference signal may be detected.

In operation S16, based on the detected phase delay, an amount of a shifted resonant wavelength of the sensing resonator is calculated. Utilizing the shift amount, the concentration of a bio-material may be calculated.

Figure 10:
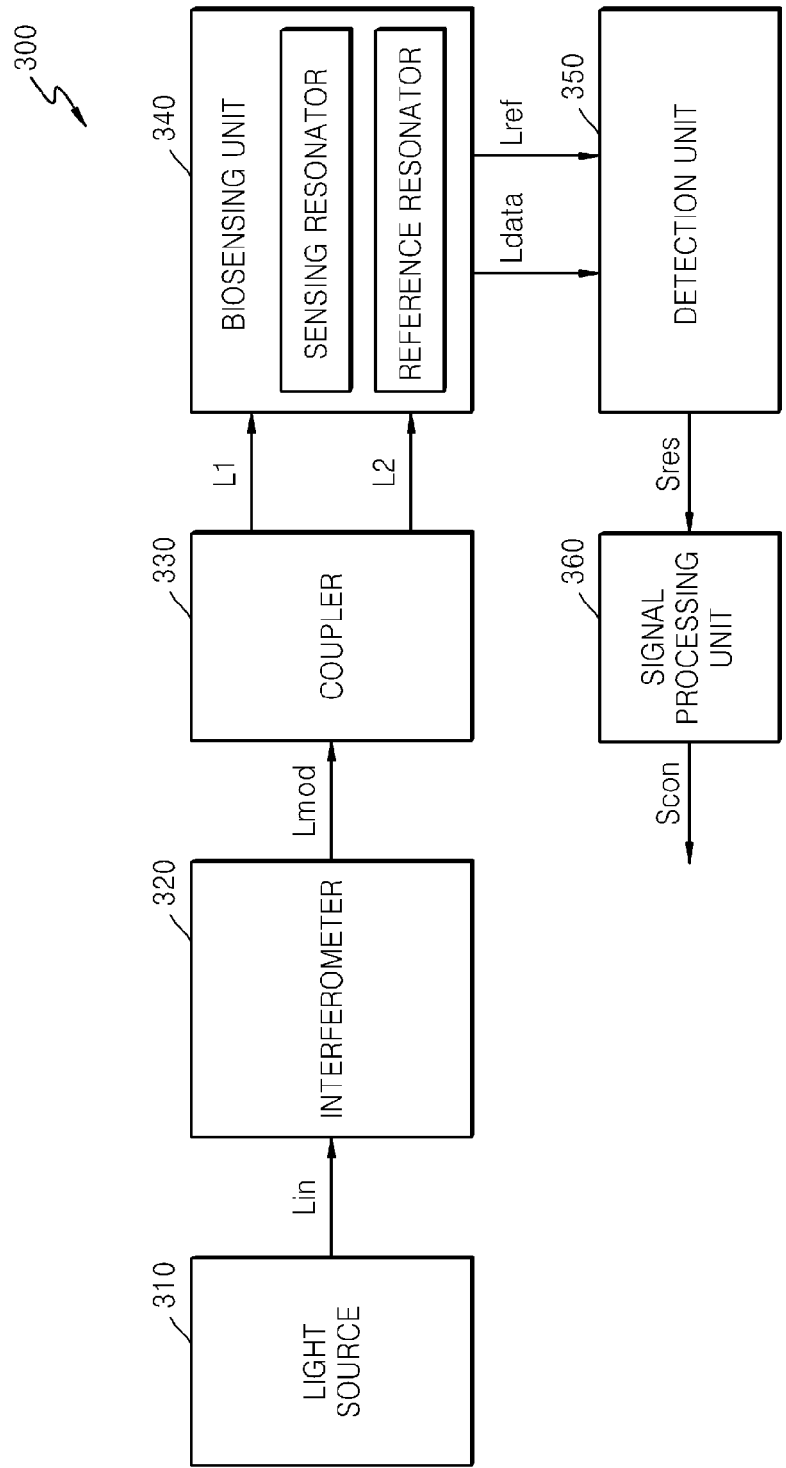
FIG. 10 is a block diagram illustrating another optical biosensor according to an example embodiment.

FIG. 10 is a block diagram illustrating another optical biosensor 300 according to an example embodiment. With regard to the optical biosensor 300 shown in FIG. 10, the same components as those shown in FIG. 1 are also operated identically or similarly to those shown in FIG. 1. Thus, their repeated description is not provided here.

As illustrated in FIG. 10, the optical biosensor 300 may include a light source 310, an interferometer 320, a coupler 330, a biosensing unit 340, a detection unit 350, and a signal processing unit 360.

Various types of light sources, for example, a broadband light source, may be used as the light source 310. Additionally, the interferometer 320 may be included so as to generate a phase-modulated light signal from the input optical signal $L_{in}$ that is generated from the light source 310. For example, a Mach-Zehnder interferometer may be used as the interferometer 320.

A light signal Lmod, which is phase-modulated from the interferometer 320, is separated into the first optical signal L1 and the second optical signal L2 via a coupler 330. The first optical signal L1 is transmitted via a first optical path that includes a sensing resonator inside the biosensing unit 340. The second optical signal L2 is transmitted via a second optical path that includes a reference resonator inside the biosensing unit 340. As the first light signal L1 passes through the sensing resonator, the sensing signal Ldata is generated. As the second light signal L2 passes through the reference resonator, the reference signal Lref is generated.

A phase delay between the sensing signal Ldata and the reference signal Lref are detected through a signal modulation operation of the detection unit 350. Then, a detection result signal Sres is provided to the signal processing unit 360. The signal processing unit 360 analyzes the detection result signal Sres, and thus, calculates an amount of a shifted resonant wavelength of the sensing resonator. Additionally, the signal processing unit 360 outputs a concentration sensing signal Scon of a bio-material according to an amount of a shifted resonant wavelength.

Figure 11:
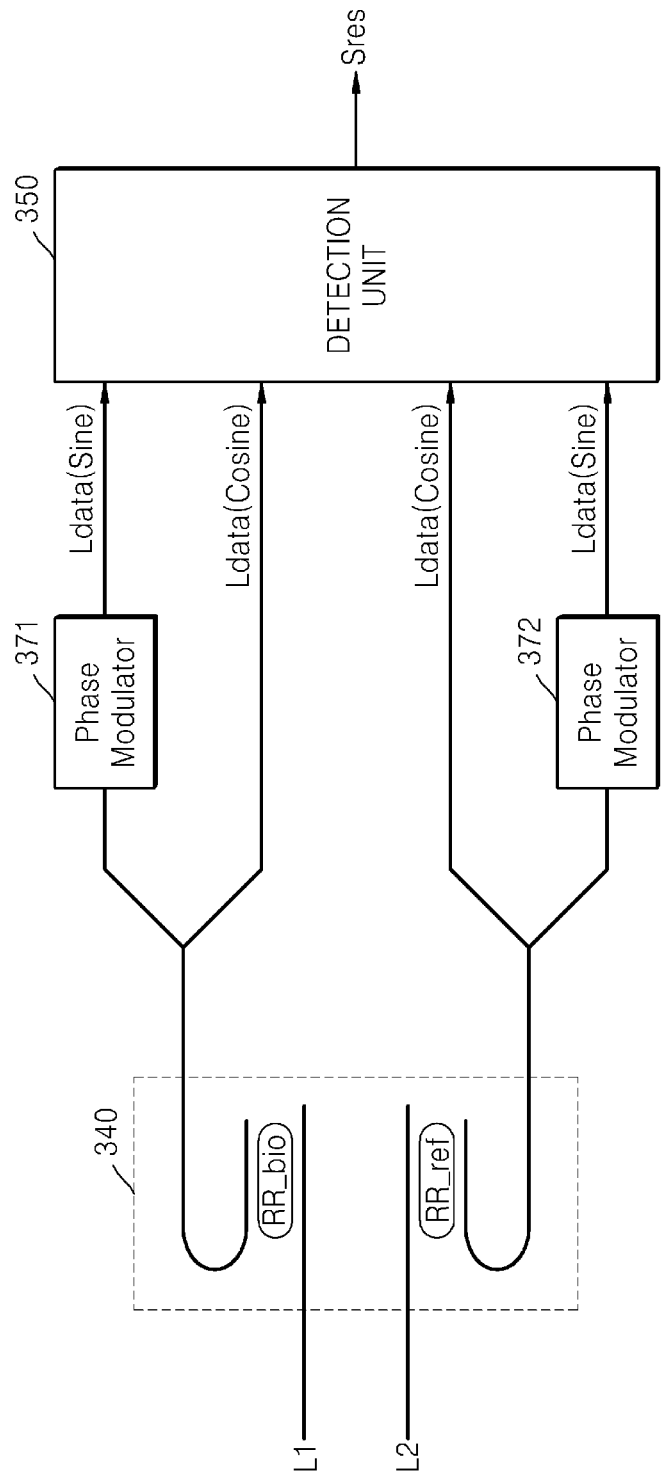
FIG. 11 is a block diagram illustrating an example of implementation of the optical biosensor of FIG. 10.

FIG. 11 is a block diagram illustrating an example of implementation of the optical biosensor 300 of FIG. 10. The biosensing unit 340 includes a sensing resonator and a reference resonator. FIG. 11 illustrates an example of implementing the resonators as a ring resonator. One or more phase modulators 371 and 372 may be included in the optical biosensor 300 for a signal demodulation operation of the detection unit 350. For example, if the sensing signal Ldata, which is generated when the first optical signal L1 passes through a sensing resonator, has characteristics of a cosine function, a sine-wave modulation signal Ldata, which is obtained by modulating a phase of the sensing signal Ldata at an angle of 90° for quadrature signal processing, is further provided to the detection unit 350. Similarly, if the reference signal Lref, which is generated when the second optical signal L2 passes through a reference resonator, has characteristics of a cosine function, a sine-wave modulation signal Lref, which is obtained by modulating a phase of the reference signal Lref at an angle of 90° is further provided to the detection unit 350.

Figure 12:
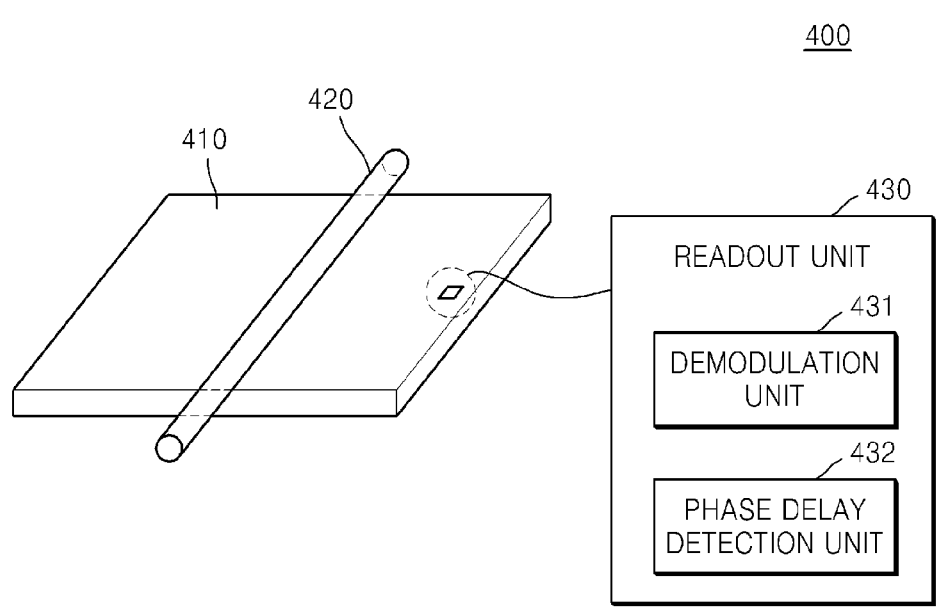
FIG. 12 is a block diagram illustrating a biosensing system according to an example embodiment.

FIG. 12 is a block diagram illustrating a biosensing system 400 according to an example embodiment.

Referring to FIG. 12, the biosensing system 400 may include a biosensor chip 410, a fluidic channel 420, and a readout unit 430. Additionally, the readout unit 430 may include one or more elements for measuring the concentration of a bio-material by processing the sensing signal Ldata and the reference signal Lref. For example, the readout unit 430 may include a demodulation unit 431 for extracting a phase element through a signal demodulation processing, and a phase delay detection unit 432 for detecting a phase delay between a sensing signal and a reference signal from the extracted phase element.

The biosensor chip 410 senses the concentration of a bio-material by using optical characteristics, and thus, outputs the sensed concentration as an electrical signal. In an example embodiment, the biosensor chip 410 may be the optical biosensor 100 of FIG. 1. If the biosensor chip 410 generates an optical signal, an additional light source is not necessary. Additionally, the concentration of the bio-material may be sensed, based on a phase delay between a sensing signal and a reference signal through a signal modulation operation, without having to performing an analysis operation by using an additional spectrometer. Thus, the biosensing system 400 may be appropriate for downsizing, low-powering, and improving mobility.

The fluidic channel 420 is a path into which a bio-material may be received and flow therethrough. The fluidic channel 420 may be aligned in a location in which an upper part of the biosensor chip 410, e.g., an opening of the biosensing chip 410 is placed. When a fluid or a gas, which contains a biomaterial, is received via the fluidic channel 420, the biomaterial may contact the biosensor chip 410 via the opening. The fluidic channel 420 may be a micro-fluidic channel, or a fluidic channel which is formed in a micro-fluidic chip. Additionally, FIG. 12 illustrates the fluidic channel 420 in a linear form. However, it should be understood that the fluidic channel 420 may be configured in various forms.

The readout unit 430 measures the concentration of a biomaterial based on an electrical signal inside the biosensor chip 410. The readout unit 430 may receive an electrical signal which is output at the biosensor chip 410 via a connection terminal and a connection line. Otherwise, the readout unit 430 may be integrated into the biosensor chip 410.

While example embodiments have been disclosed herein, it should be understood that other variations may be possible. Such variations are not to be regarded as a departure from the spirit and scope of example embodiments of the present application, and all such modifications as would be obvious to one skilled in the art are intended to be included within the scope of the following claims.

What is claimed is:

1. An optical biosensor comprising:
a biosensing unit configured to receive first and second optical signals originating from a phase-modulated optical signal, to output a sensing signal via transmission of the first optical signal through a first optical path that includes a sensing resonator, and to output a reference signal via transmission of the second optical signal through a second optical path that includes a reference resonator;
a detection unit configured to receive the sensing signal and the reference signal, to detect a first phase element of the sensing signal and a second phase element of the reference signal through a signal demodulation operation, and to detect a phase difference between the sensing signal and the reference signal according to the first phase element and the second phase element;
a signal processing unit configured to calculate a concentration of a bio-material based on the phase difference; and
a quadrature signal generation unit configured to supply a quadrature signal to the detection unit, the quadrature signal having a phase which is in quadrature with respect to the sensing signal and the reference signal.

2. The optical biosensor of claim 1, wherein the first optical signal and the second optical signal have a same phase.

3. The optical biosensor of claim 1, wherein the sensing resonator is configured such that a resonant wavelength thereof changes when the bio-material is combined with the sensing resonator, and the phase difference has a value that corresponds to an amount of change of the resonant wavelength of the sensing resonator.

4. The optical biosensor of claim 1, wherein the detection unit is configured to receive a first quadrature signal and a second quadrature signal from the quadrature signal generation unit, to detect the first phase element of the sensing signal via performance of a first operation on the sensing signal and the first quadrature signal, and to detect the second phase element of the reference signal via performance of a second operation on the reference signal and the second quadrature signal.

5. The optical biosensor of claim 4, wherein the detection unit is configured such that the performance of the first operation includes a division of the first quadrature signal into the sensing signal and an execution of an arctangent operation on a result of the division.

6. The optical biosensor of claim 4, wherein the detection unit is configured to receive a clock signal having a known frequency and to output a counting result of the clock signal, the counting result corresponding to the phase difference between the sensing signal and the reference signal.

7. The optical biosensor of claim 1, further comprising:
a light source configured to generate an optical signal; and
an interferometer configured to receive the optical signal and modulate a phase of the optical signal to generate the phase-modulated optical signal.

8. The optical biosensor of claim 1, further comprising:
a database unit configured to store information regarding the concentration of the bio-material in connection with the phase difference.

9. A method of operating an optical biosensor, the method comprising:
receiving first and second optical signals originating from a phase-modulated optical signal;
outputting a sensing signal by transmitting the first optical signal via a first optical path that includes a sensing resonator;
outputting a reference signal by transmitting the second optical signal via a second optical path that includes a reference resonator;
detecting a first phase element of the sensing signal and a second phase element of the reference signal through a signal demodulation operation;
detecting a phase difference between the sensing signal and the reference signal according to the first phase element and the second phase element;
calculating a concentration of a bio-material based on the phase difference; and
generating first and second quadrature signals having a phase which is in quadrature with respect to the sensing signal and the reference signal.

10. The method of claim 9, wherein the receiving includes the first optical signal and the second optical signal having a same phase.

11. The method of claim 9, wherein the outputting a sensing signal includes combining the bio-material with the sensing resonator, a resonant wavelength of the sensing resonator changing with the combining, the phase difference having a value that corresponds to an amount of change of the resonant wavelength of the sensing resonator.

12. The method of claim 9,
wherein the detecting a first phase element of the sensing signal and a second phase element of the reference signal includes performing a first operation on the sensing signal and the first quadrature signal to detect the first phase element of the sensing signal and performing a second operation on the reference signal and the second quadrature signal to detect the second phase element of the reference signal.

13. The method of claim 9, further comprising:
generating an optical signal; and
modulating a phase of the optical signal with an interferometer to generate the phase-modulated optical signal.

14. The method of claim 9, wherein the calculating includes accessing a storage unit in which the concentration of the bio-material is databased and stored in connection with the phase difference.

15. An optical biosensor comprising:
a biosensing unit including a first optical path and a second optical path, the first optical path including a sensing resonator configured to be exposed to a bio-material, the second optical path including a reference resonator configured to be isolated from the bio-material, the first optical path configured to receive a first phase-modulated optical signal and to output a sensing signal, the second optical path configured to receive a second phase-modulated optical signal and to output a reference signal;
a detection unit connected to the biosensing unit, the detection unit configured to demodulate the sensing signal and the reference signal to detect a phase difference therebetween, the detection unit including,
a quadrature signal generation unit,
a demodulation unit, and
a phase delay calculation unit; and
a signal processing unit connected to the detection unit, the signal processing unit configured to calculate a concentration of the bio-material based on the phase difference between the sensing signal and the reference signal.

16. The optical biosensor of claim 15, wherein the first optical path includes a first optical waveguide and a second optical waveguide, the sensing resonator arranged between the first optical waveguide and the second optical waveguide.

17. The optical biosensor of claim 16, wherein the sensing resonator is spaced apart from the first optical waveguide by a first gap and spaced apart from the second optical waveguide by a second gap.

18. The optical biosensor of claim 15, further comprising:
a coupler connected to the biosensing unit, the coupler configured to divide a phase-modulated input optical signal into the first phase-modulated optical signal and the second phase-modulated optical signal for transmission to the biosensing unit.

* * * * *